US010557755B2

(12) United States Patent
Suzuki et al.

(10) Patent No.: US 10,557,755 B2
(45) Date of Patent: Feb. 11, 2020

(54) POSITION DETECTION METHOD AND OPTICAL MODULE

(71) Applicant: HAMAMATSU PHOTONICS K.K., Hamamatsu-shi, Shizuoka (JP)

(72) Inventors: Tomofumi Suzuki, Hamamatsu (JP); Kyosuke Kotani, Hamamatsu (JP)

(73) Assignee: HAMAMATSU PHOTONICS K.K., Hamamatsu-Shi, Shizuoka (JP)

( * ) Notice: Subject to any disclaimer, the term of this patent is extended or adjusted under 35 U.S.C. 154(b) by 0 days.

(21) Appl. No.: 15/792,984

(22) Filed: Oct. 25, 2017

(65) Prior Publication Data

US 2018/0120156 A1     May 3, 2018

(30) Foreign Application Priority Data

Oct. 27, 2016    (JP) ................................ 2016-210890

(51) Int. Cl.
    *G01J 3/02*         (2006.01)
    *H04L 27/26*      (2006.01)
    (Continued)

(52) U.S. Cl.
    CPC ........ *G01J 3/0289* (2013.01); *G01B 9/02015* (2013.01); *G01D 5/266* (2013.01); *G01J 3/0256* (2013.01); *G01J 3/4532* (2013.01); *G01J 3/4535* (2013.01); *G01N 21/95* (2013.01); *G02B 27/108* (2013.01); *H04L 27/2628* (2013.01); *B81B 7/0067* (2013.01); *B81B 2201/042* (2013.01); *G01N 2021/9511* (2013.01)

(58) Field of Classification Search
CPC ...... G01J 3/0289; G01J 3/4532; G01J 3/4535; G02B 27/108; H04L 27/2628
See application file for complete search history.

(56) References Cited

U.S. PATENT DOCUMENTS 4,537,508 A * 8/1985 Doyle .................... G01J 3/453
                                                    356/452
4,932,780 A * 6/1990 Izumi ................... G01J 3/0213
                                                    356/451

(Continued)

FOREIGN PATENT DOCUMENTS

JP        2010-170029 A      8/2010

*Primary Examiner* — Dominic J Bologna
*Assistant Examiner* — Violeta A Prieto
(74) *Attorney, Agent, or Firm* — Drinker Biddle & Reath LLP

(57) ABSTRACT

Provided is a position detection method including splitting detection light into first and second light, the first light being incident on a returning optical path, a portion of the first light being transmitted through a beam splitter and a remaining portion of the first light being reflected by the beam splitter to reach the beam splitter through a movable mirror every time the first light reaches the beam splitter through the movable mirror, combining the first light transmitted though the beam splitter and the second light to generate multiple interference light, extracting a second interference light signal having a wavelength of 1/p (p is a natural number) of a wavelength of detection light from a first interference light signal of the multiple interference light, and calculating a position of the movable portion in a predetermined direction based on the second interference light signal.

9 Claims, 9 Drawing Sheets

(51) Int. Cl.
*G02B 27/10* (2006.01)
*G01N 21/95* (2006.01)
*B81B 7/00* (2006.01)
*G01B 9/02* (2006.01)
*G01D 5/26* (2006.01)
*G01J 3/453* (2006.01)

(56) References Cited

U.S. PATENT DOCUMENTS

| | | | |
|---|---|---|---|
| 6,233,054 B1* | 5/2001 | Theriault | G01J 3/45 356/451 |
| 10,422,696 B2* | 9/2019 | Warashina | G01J 3/02 |
| 2002/0109851 A1* | 8/2002 | Deck | G01B 11/06 356/512 |
| 2003/0164951 A1* | 9/2003 | Deck | G01J 9/0246 356/519 |
| 2010/0188728 A1* | 7/2010 | Warashina | B81B 7/0067 359/290 |
| 2010/0265512 A1* | 10/2010 | Medhat | G02B 5/124 356/455 |
| 2011/0058180 A1* | 3/2011 | Khalil | G01J 3/02 356/521 |
| 2018/0195853 A1* | 7/2018 | Warashina | G01J 3/45 |
| 2018/0217001 A1* | 8/2018 | Warashina | G01J 3/45 |
| 2019/0033136 A1* | 1/2019 | Warashina | G01J 3/02 |

* cited by examiner

POSITION DETECTION METHOD AND OPTICAL MODULE

TECHNICAL FIELD

The present disclosure relates to a position detection method and an optical module.

BACKGROUND

Japanese Unexamined Patent Publication No. 2010-170029 describes an optical module in which an interference optical system is formed on a silicon on insulator (SOI) substrate by micro electro mechanical systems (MEMS) technology. Such an optical module has attracted attention because it can provide a compact, low-cost Fourier transform infrared spectroscopic analyzer (FTIR).

SUMMARY

In the optical module as described above, it is required to detect a position of a measurement mirror which constitutes an interference optical system for measurement, in other words, a position of a movable portion provided with the measurement mirror with accuracy according to a request. This is because the positional accuracy of the measurement mirror is particularly important in determining main parameters of a spectrometer such as wavelength reproducibility, wavelength resolution, and an S/N ratio.

Therefore, one aspect of the present disclosure is to provide a position detection method and an optical module capable of detecting a position of a movable portion with accuracy according to a request.

According to the present disclosure, there is provided a position detection method for detecting a position of a movable portion which moves along a predetermined direction, including: splitting detection light into first light and second light in an interference optical system including a movable mirror provided with the movable portion and a beam splitter of which position is fixed; the first light being incident on a returning optical path formed in the interference optical system by the movable mirror and the beam splitter; a portion of the first light being transmitted through the beam splitter and a remaining portion of the first light being reflected by the beam splitter to reach the beam splitter through the movable mirror every time the first light reaches the beam splitter through the movable mirror in the returning optical path; combining the first light transmitted through the beam splitter from the returning optical path and the second light to generate multiple interference light in the interference optical system; extracting a second interference light signal having a wavelength of 1/p (p is a natural number) of a wavelength of the detection light from a first interference light signal of the multiple interference light; and calculating the position of the movable portion in the predetermined direction based on the second interference light signal.

In the position detection method, every time the first light reaches the beam splitter through the movable mirror in the returning optical path, a portion of the first light is transmitted through the beam splitter, the remaining portion of the first light is reflected by the beam splitter, and the first light reaches the beam splitter again through the movable mirror. Therefore, every time the first light reaches the beam splitter, the number of times of reciprocation of the first light as a component along the predetermined direction in which the movable portion moves increases, and an optical path difference occurs in the first light by an amount corresponding to the position of the movable portion in the predetermined direction. For this reason, when the first light transmitted through the beam splitter and the second light are combined, the multiple interference light is generated. The second interference light signal having a wavelength of 1/p (p is a natural number) of the wavelength of the detection light is extracted from the first interference light signal of the multiple interference light. The position of the movable portion in the predetermined direction is calculated based on the second interference light signal. As the wavelength (period) of the second interference light signal becomes shorter, the resolution of position detection based on the second interference light signal becomes higher. Therefore, by selecting the wavelength of the second interference light signal to be extracted, it is possible to detect the position of the movable portion with accuracy according to a request.

In the position detection method according to the present disclosure, in extracting the second interference light signal, a light spectrum having a peak at each wavelength of 1/q (q is a natural number) of the wavelength of the detection light may be acquired by Fourier-transforming the first interference light signal, and the second interference light signal may be acquired by inverse-Fourier-transforming the light spectrum with respect to one peak. According to this, because the wavelength of the second interference light signal becomes shorter as the wavelength of the peak used for the inverse Fourier transform becomes shorter, by selecting the peak used for the inverse Fourier transform, it is possible to detect the position of the movable portion with accuracy according to a request.

In the position detection method according to the present disclosure, p may be an integer of 2 or more. According to this, because the wavelength of the second interference light signal is shorter than the wavelength of the detection light, it is possible to detect the position of the movable portion with higher accuracy.

In the position detection method according to the present disclosure, the interference optical system may further include a fixed mirror of which position is fixed, and the returning optical path may be formed in the interference optical system by the movable mirror, the beam splitter, and the fixed mirror and have a rectangular shape when viewed from a direction perpendicular to a plane where the returning optical path is located. According to this, it is possible to form the returning optical path in the interference optical system preferably.

In the position detection method according to the present disclosure, the detection light may be split into the first light and the second light by the beam splitter. According to this, the configuration of the interference optical system can be simplified.

According to the present disclosure, there is provided an optical module including a movable portion which moves along a predetermined direction; and an interference optical system including a movable mirror provided with the movable portion and a beam splitter of which position is fixed, wherein, in the interference optical system, a returning optical path is formed by the movable mirror and the beam splitter, and wherein, in the interference optical system, detection light is split into first light and second light, the first light is incident on the returning optical path, in the returning optical path, every time the first light reaches the beam splitter through the movable mirror, a portion of the first light is transmitted through the beam splitter, and a remaining portion of the first light is reflected by the beam splitter to reach the beam splitter through the movable mirror, and the first light transmitted through the beam splitter from the returning optical path and the second light are combined to generate multiple interference light.

In this optical module, every time the first light reaches the beam splitter through the movable mirror in the returning optical path, a portion of the first light is transmitted through the beam splitter, the remaining portion of the first light is reflected by the beam splitter, and the first light reaches the beam splitter through the movable mirror. Therefore, every time the first light reaches the beam splitter through the movable mirror, the number of times of reciprocation the first light as a component along the predetermined direction in which the movable portion moves increases, and an optical path difference occurs between the first light and the second light by an amount corresponding to the position of the movable portion in the predetermined direction. For this reason, when the first light transmitted through the beam splitter and the second light are combined, the multiple interference light is generated. The second interference light signal having a wavelength of 1/p (p is a natural number) wavelength of the detection light can be extracted from the first interference light signal of the multiple interference light. The position of the movable portion in the predetermined direction can be calculated based on the second interference light signal. As the wavelength (period) of the second interference light signal becomes shorter, the resolution of position detection based on the second interference light signal becomes higher. Therefore, by selecting the wavelength of the second interference light signal to be extracted, it is possible to detect the position of the movable portion with accuracy according to a request.

In the optical module according to the present disclosure, the interference optical system may further include a fixed mirror of which position is fixed, the returning optical path is formed in the interference optical system by the movable mirror, the beam splitter and the fixed mirror, and the returning optical path may have a rectangular shape when viewed from a direction perpendicular to a plane on which the returning optical path is located. According to this, it is possible to form the returning optical path in the interference optical system preferably.

In the optical module according to the present disclosure, in the interference optical system, the detection light may be split into the first light and the second light by the beam splitter. According to this, the configuration of the interference optical system can be simplified.

The optical module according to the present disclosure may further includes a measurement interference optical system having a measurement mirror provided with the movable portion, the measurement mirror is provided at one end portion of the movable portion in a predetermined direction, and the movable mirror is provided at the other end portion of the movable portion in a predetermined direction. According to this, it is possible to move the movable portion along the predetermined direction with well balance.

According to the present disclosure, it is possible to detect the position of the movable portion with accuracy according to a request.

DETAILED DESCRIPTION

Figure 1:
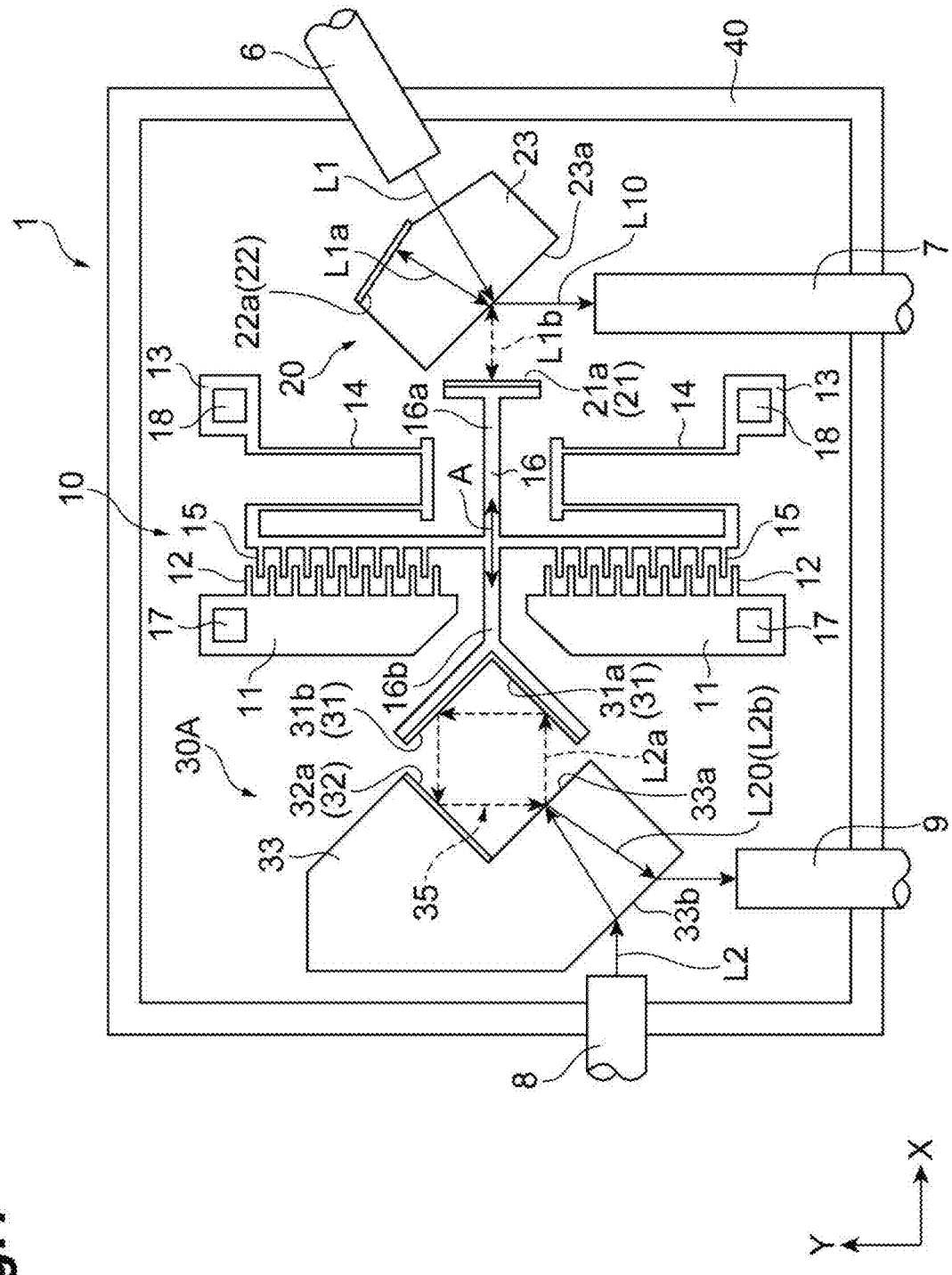
FIG. 1 is a plan view of an optical module according to an embodiment.

Hereinafter, an embodiment of the present disclosure will be described in detail with reference to the drawings. In the following description, the same reference numerals are used for the same or corresponding components, and redundant descriptions are omitted.

As illustrated in FIG. 1, the optical module 1 is configured to include an actuator 10, a first interference optical system (measurement interference optical system) 20, a second interference optical system (interference optical system) 30A, and a frame 40. The optical module 1 is a MEMS device formed by an SOI substrate. In other words, the optical module 1 is configured to include a substrate, an insulating layer formed on the substrate, and a semiconductor layer formed over the insulating layer. The substrate and the semiconductor layer are made of silicon, and the insulating layer is made of a silicon oxide. The actuator 10, the first interference optical system 20, the second interference optical system 30A, and the frame 40 are mainly formed on the substrate by a portion of the semiconductor layer. The frame 40 surrounds the actuator 10, the first interference optical system 20, and the second interference optical system 30A and is fixed to the substrate through an insulating layer.

The actuator 10 is an electrostatic actuator and is configured to include a pair of first fixed portions 11, a first comb-teeth portion 12, a pair of second fixed portions 13, a support portion 14, a second comb-teeth portion 15, and a movable portion 16.

The pair of first fixed portions 11 are arranged side by side in the Y-axis direction and are fixed to the substrate through the insulating layer. The first comb-teeth portion 12 is provided on a side surface on one side of each first fixed portion 11. The first comb-teeth portion 12 is in a state of floating with respect to the substrate by removing the insulating layer directly thereunder. The first fixed portion 11 and the first comb-teeth portion 12 are integrally formed by a portion of the semiconductor layer. A first electrode 17 is provided with each of the first fixed portions 11.

The pair of second fixed portions 13 are arranged side by side in the Y-axis direction and are fixed to the substrate through the insulating layer. The pair of second fixed portions 13 are disposed on the one side with respect to the pair of first fixed portions 11. The support portion 14 is stretched between each of the second fixed portions 13 and the movable portion 16. The second comb-teeth portion 15 is provided on the support portion 14 so that each comb-tooth thereof is positioned between the comb teeth of the first comb-teeth portion 12. The movable portion 16 extends along the X-axis direction so as to pass between the pair of first fixed portions 11 and between the pair of second fixed portions 13. The support portion 14, the second comb-teeth portion 15, and the movable portion 16 are in a floating state with respect to the substrate by removing the insulating layer directly thereunder. The second fixed portions 13, the support portion 14, the second comb-teeth portion 15, and the movable portion 16 are integrally formed by a portion of the semiconductor layer. A second electrode 18 is provided with each of the second fixed portions 13.

Because the support portion 14 has a structure in which leaf springs are connected to each other, the movable portion 16 is movable along a direction (predetermined direction) A parallel to the X axis. The support portion 14 exerts an elastic force on the movable portion 16 so that the movable portion 16 returns to an initial position. Therefore, when a voltage is applied between the first electrode 17 and the second electrode 18, a electrostatic attractive force is exerted between the first comb-teeth portion 12 and the second comb-teeth portion 15 in accordance with the voltage (potential difference), the movable portion 16 is moved along the direction A to a position where the electrostatic attractive force and the elastic force by the support portion 14 are balanced.

The first interference optical system 20 is configured to include a first movable mirror (measurement mirror) 21, a first fixed mirror 22, and an optical block 23 and constitutes a Michelson interference optical system. Measurement light L1 is incident on the first interference optical system 20 through a measurement light incident portion 6, and interference light L10 of the measurement light L1 is emitted from the first interference optical system 20 through a measurement light emitting portion 7. The measurement light incident portion 6 and the measurement light emitting portion 7 are, for example, optical fibers and are fixed to the frame 40.

The first movable mirror 21 is provided at one end portion 16a of the movable portion 16 in the direction A. The first movable mirror 21 has a reflecting surface 21a. The reflecting surface 21a is a surface perpendicular to the direction A. The first fixed mirror 22 is provided on one side surface of the optical block 23. In other words, the position of the first fixed mirror 22 is fixed. The first fixed mirror 22 has a reflecting surface 22a. The reflecting surface 22a is a surface perpendicular to the XY plane and is inclined at a predetermined angle with respect to the direction A. The optical block 23 is formed by a portion of the semiconductor layer and is fixed to the substrate through the insulating layer. The side surface of the optical block 23 on the side of the first movable mirror 21 functions as a first beam splitter 23a. In other words, the position of the first beam splitter 23a is fixed. The first beam splitter 23a is a surface perpendicular to the XY plane and is inclined by 45 degrees with respect to the direction A.

The measurement light L1 incident on the first interference optical system 20 through the measurement light incident portion 6 travels through the optical block 23 and is split into light toward the first movable mirror 21 and light toward the first fixed mirror 22 by the first beam splitter 23a. The measurement light L1a split toward the first fixed mirror 22 is reflected by the reflecting surface 22a of the first fixed mirror 22 and returns to the first beam splitter 23a on the same optical path. On the other hand, the measurement light L1b split toward the first movable mirror 21 along the direction A is reflected by the reflecting surface 21a of the first movable mirror 21 and returns to the first beam splitter 23a on the same optical path. The measurement light L1a and the measurement light L1b returning to the first beam splitter 23a are combined by the first beam splitter 23a and become the interference light L10 of the measurement light. The interference light L10 of the measurement light is emitted from the first interference optical system 20 through the measurement light emitting portion 7.

The second interference optical system 30A is configured to include a second movable mirror 31, a second fixed mirror 32, and an optical block 33 and constitutes a Michelson interference optical system. Detection light L2 is incident on the second interference optical system 30A through a detection light incident portion 8, and interference light L20 of the detection light L2 is emitted from the second interference optical system 30A through a detection light emitting portion 9. The detection light L2 is, for example, a laser beam and is output from a laser light source such as a semiconductor laser prepared outside the optical module 1. The detection light incident portion 8 and the detection light emitting portion 9 are, for example, optical fibers and are fixed to the frame 40.

The second movable mirror 31 is provided at the other end portion 16b of the movable portion 16 in the direction A. The second movable mirror 31 has reflecting surfaces 31a and 31b. The reflecting surface 31a is a surface perpendicular to the XY plane and is inclined by 45 degrees with respect to the direction A. The reflecting surface 31b is a surface perpendicular to the XY plane and is inclined by 45 degrees with respect to the direction A on the side opposite to the reflecting surface 31a. The second fixed mirror 32 is provided on one side surface of the optical block 33. In other words, the position of the second fixed mirror 32 is fixed. The second fixed mirror 32 has a reflecting surface 32a. The reflecting surface 32a extends parallel to the reflecting surface 31a and faces the reflecting surface 31b in the direction A.

The optical block 33 is formed by a portion of the semiconductor layer and is fixed to the substrate through the insulating layer. The side surface of the optical block 33 facing the reflecting surface 32a functions as a second beam splitter 33a. In other words, the position of the second beam splitter 33a is fixed. The second beam splitter 33a extends parallel to the reflecting surface 31b and faces the reflecting surface 31a in the direction A. The side surface of the optical block 33 facing the second beam splitter 33a functions as a refracting surface 33b. The refracting surface 33b extends parallel to the second beam splitter 33a.

In the second interference optical system 30A, a returning optical path (circulating optical path) 35 is formed by the second movable mirror 31, the second fixed mirror 32, and the second beam splitter 33a. The detection light L2 is incident on the returning optical path 35 at a predetermined incident position in the second beam splitter 33a. The detection light L2 incident on the returning optical path 35 travels on the returning optical path 35 and returns to the incident position of the second beam splitter 33a through the second movable mirror 31 and the second fixed mirror 32.

The returning optical path 35 includes at least an optical path in which the detection light L2 reciprocates as a component along the direction A. In other words, the detection light L2 incident on the returning optical path 35 reciprocates at least once over a component along the direction A every time the detection light travels on the returning optical path 35 and reaches the second beam splitter 33a. Herein, the optical path reciprocating "as a component along the direction A" denotes that the optical path has a component along the direction A. In this embodiment, the returning optical path 35 has a rectangular shape (i.e. rectangular annular shape or looping rectangular shape) when viewed from a direction perpendicular to the XY plane where the returning optical path 35 is located. The returning optical path 35 includes two pairs of optical paths facing each other. One pair of optical paths extend parallel to direction A, and the other pair of optical paths extend perpendicular to direction A. In this returning optical path 35, the detection light L2 reciprocates once along the direction A between the second beam splitter 33a and the second movable mirror 31 every time the detection light reaches the second beam splitter 33a.

After the detection light L2 incident on the second interference optical system 30A along the direction A through the detection light incident portion 8 is refracted by the refracting surface 33b of the optical block 33, the detection light travels through the optical block 33 and is split into first light L2a and second light L2b by the second beam splitter 33a (first step). The first light L2a is light transmitted through the second beam splitter 33a and is incident on the returning optical path 35 and travels toward the second movable mirror 31 along the direction A (second step). The second light L2b is light reflected by the second beam splitter 33a and is not incident on the returning optical path 35. The first light L2a traveling toward the second movable mirror 31 along the direction A is sequentially reflected by the reflecting surface 31a and the reflecting surface 31b of the second movable mirror 31 and travels toward the second fixed mirror 32 along the direction A. The first light L2a traveling toward the second fixed mirror 32 along the direction A is reflected by the reflecting surface 32b of the second fixed mirror 32 and reaches the second beam splitter 33a.

A portion of the first light L2a that has reached the second beam splitter 33a is transmitted through the second beam splitter 33a. On the other hand, the remaining portion of the first light L2a that has reached the second beam splitter 33a is sequentially reflected by the reflecting surface 31a and the reflecting surface 31b of the second movable mirror 31 and the reflecting surface 32b of the second fixed mirror 32 and reaches the second beam splitter 33a. In this manner, in the returning optical path 35, every time the first light L2a reaches the second beam splitter 33a through the second movable mirror 31, a portion of the first light L2a is transmitted through the second beam splitter 33a, and the remaining portion of the first light L2a is reflected by the second beam splitter 33a and reaches the second beam splitter 33a through the second movable mirror 31 (third step).

The first light L2a that has been transmitted through the second beam splitter 33a from the returning optical path 35 and the second light L2b are combined by the second beam splitter 33a and become the interference light L20 of the detection light L2 (fourth step). Herein, in the third step, every time the first light L2a reaches the second beam splitter 33a, the number of times of reciprocation of the first light L2a as a component along the direction A increases, and an optical path difference occurs in the first light L2a by an amount corresponding to the position of the second movable mirror 31 (that is, the position of the movable portion 16) in the direction A. More specifically, every time the first light L2a reaches the second beam splitter 33a, an optical path difference occurs in the first light L2a by twice the moving distance x of the movable portion 16. For this reason, the interference light L20 of the detection light L2 becomes multiple interference light which is interference light of the first light L2a including the optical path difference components of 2x, 4x, 6x, . . . and the second light L2b. After the interference light L20 of the detection light L2 is refracted by the refracting surface 33b of the optical block 33, the interference light is emitted from the second interference optical system 30A along the direction perpendicular to the direction A through the detection light emitting portion 9.

Figure 2:
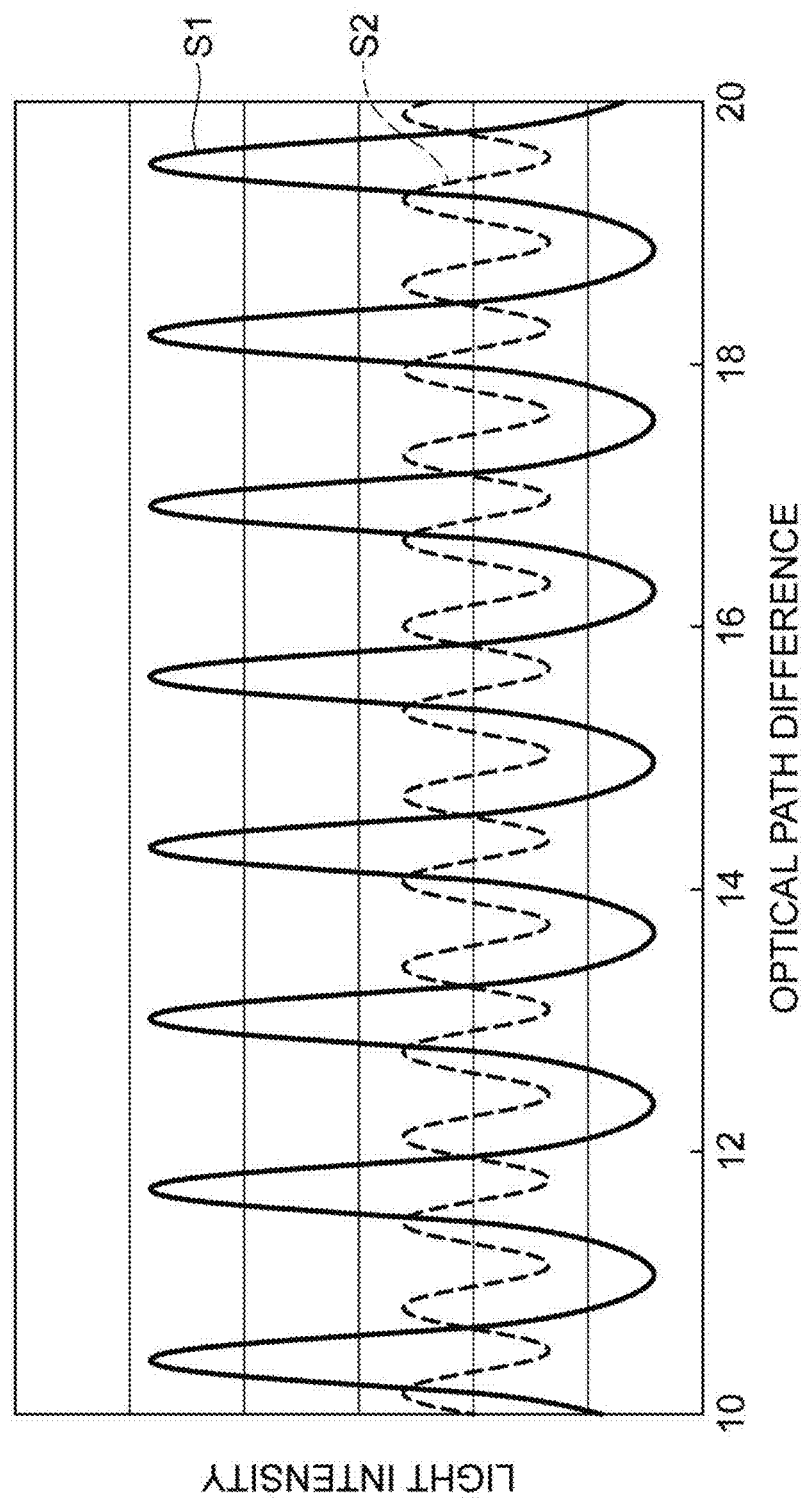
FIG. 2 is a diagram illustrating examples of a first interference light signal and a second interference light signal.

The interference light L20 of the detection light L2 emitted from the detection light emitting portion 9 is detected by, for example, a light detector prepared outside the optical module 1. Therefore, as illustrated in FIG. 2, the first interference light signal S1 of the multiple interference light is acquired. The intensity I of the first interference light signal S1 is represented by the following Mathematical Formula (1). In Mathematical Formula (1), m is the number of times of transmission of the first light L2a through the returning optical path 35, B(m) is an intensity of the interference light between the first light L2a and the second light L2b when the number of times of transmission is m, v is a wave number of the detection light L2, a is an optical path difference constant, and n is a refractive index of air. The optical path difference constant a is a constant representing how many times the optical path difference occurs with respect to the moving distance x of the movable portion 16 every time the first light L2a reaches the second beam splitter 33a in the returning optical path 35. In this embodiment, because the first light L2a reciprocates once in the direction A every time the light reaches the second beam splitter 33a, the optical path difference constant a is a value 2.

[Mathematical Formula 1]

$$1(x) = \Sigma_{m=0}^{\infty} B(m) \cos 2\pi v manx \tag{1}$$

Figure 3:
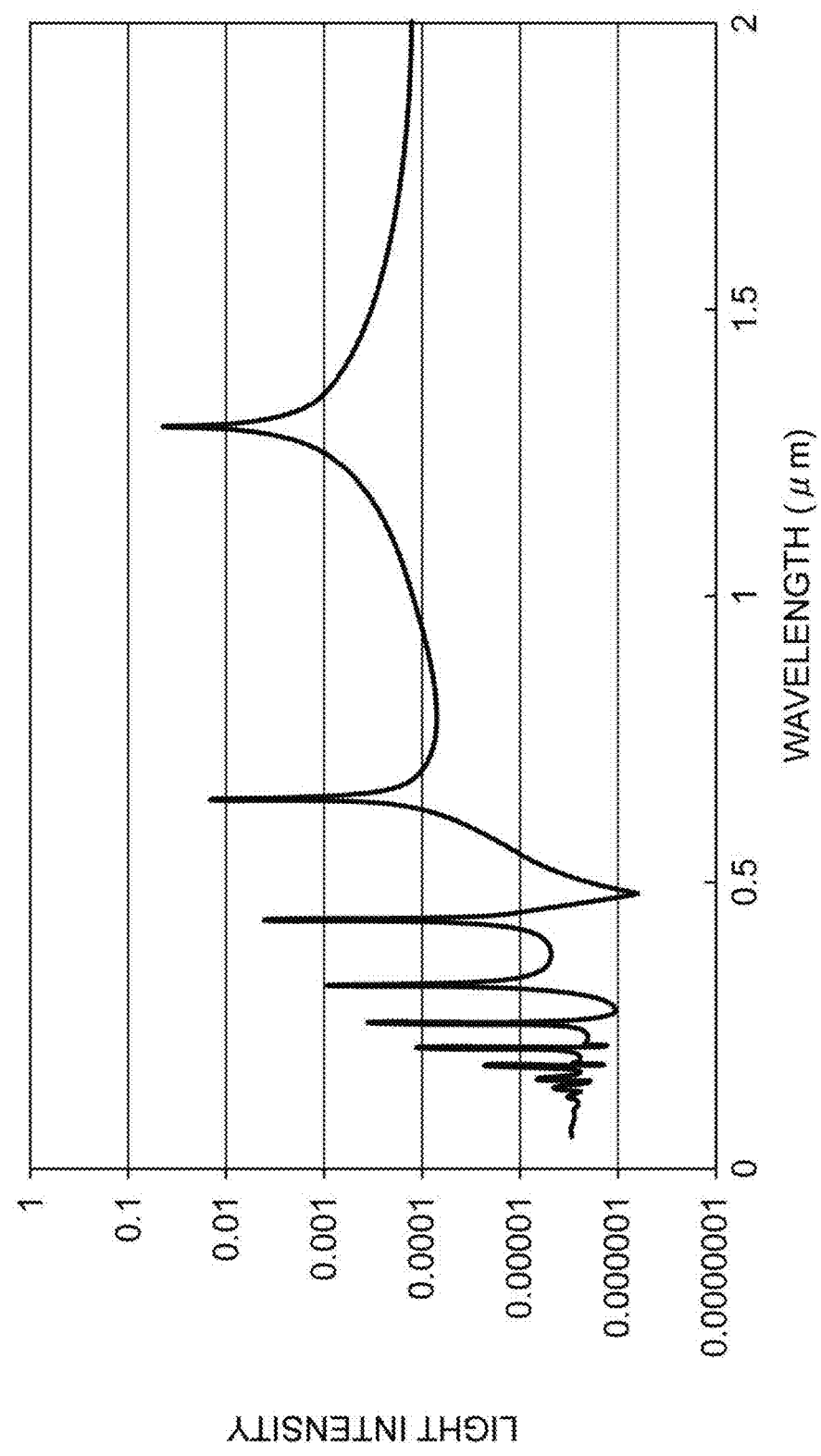
FIG. 3 is a diagram illustrating a light spectrum acquired by Fourier-transforming the first interference light signal in FIG. 2.

Subsequently, a light spectrum having a peak at each wavelength of 1/q (q is a natural number) of the wavelength of the detection light L2 is acquired by Fourier-transforming the first interference light signal S1 (fifth step). In the example of FIG. 3, the wavelength λ of the detection light L2 is about 1.3 μm, and the light spectrum has peaks at λ, λ/2, λ/3, . . . . The calculation for Fourier-transforming the first interference light signal S1 is executed by, for example, a calculation device prepared outside the optical module 1. This calculation device is, for example, a computer having a central processing unit (CPU), read only memory (ROM), random access memory (RAM), and the like. Similarly, the following operations may be executed by this calculation device.

Subsequently, the light spectrum is inverse-Fourier-transformed with respect to any one peak, so that the second interference light signal S2 is acquired (fifth step). More specifically, in the light spectrum, data in which only a wavelength band including the wavelength of one of the peaks is left while the other wavelength bands are cut is inverse-Fourier-transformed. Therefore, the second interference light signal S2 having a wavelength (period) corresponding to the wavelength of the peak is acquired. In this embodiment, the light spectrum is inverse-Fourier-transformed with respect to a peak having the p-th longest wavelength (p is an integer of 2 or more). Therefore, the second interference light signal S2 having a period of 1/p of the period of the detection light L2 is acquired. In FIG. 2, the second interference light signal S2 acquired by inverse-Fourier-transforming the light spectrum of FIG. 3 is illustrated at the peak having the second longest wavelength. The period of the second interference light signal S2 is ½ of the period of the detection light L2.

Figure 4:
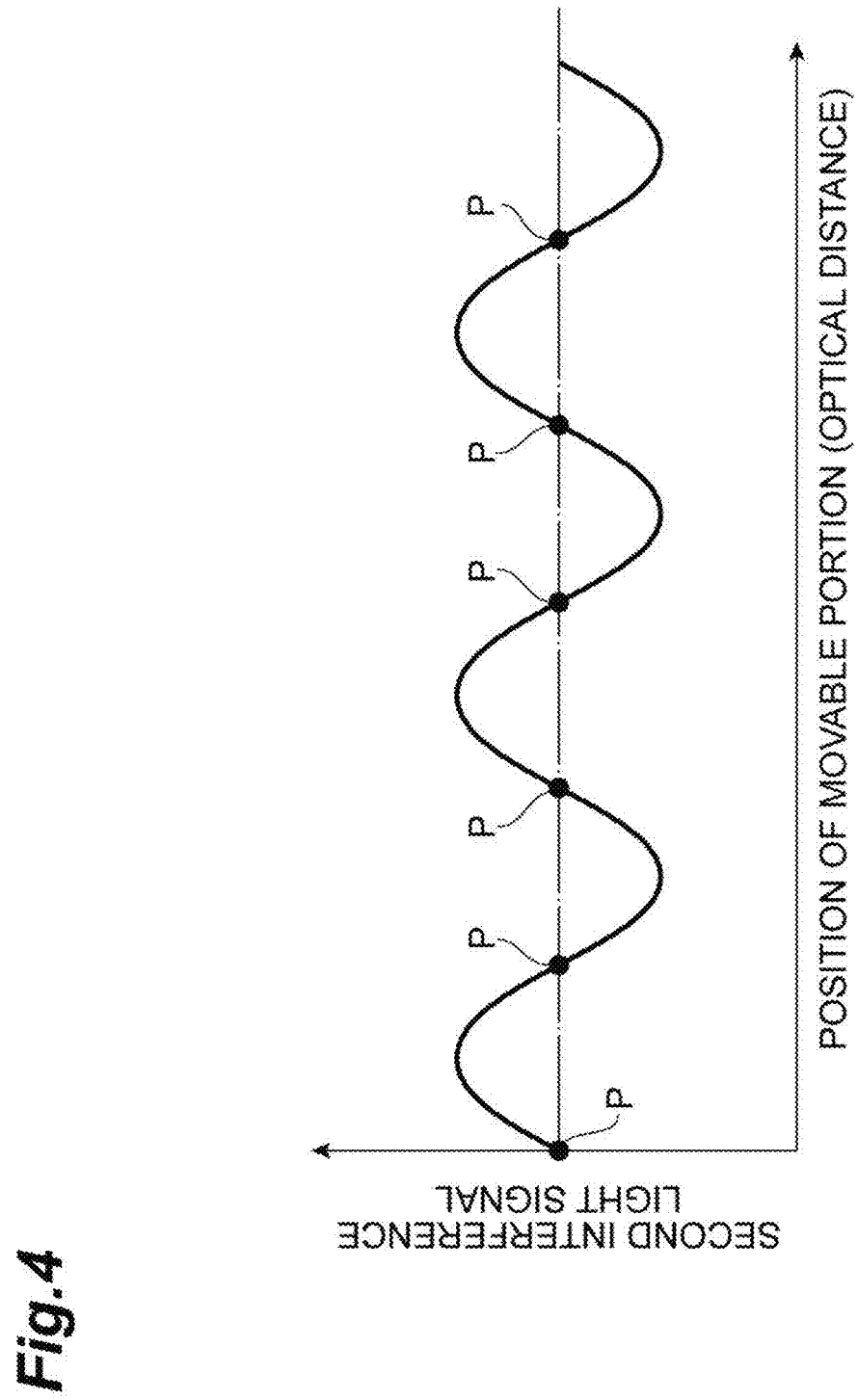
FIG. 4 is a diagram illustrating a relationship between a position (optical distance) of a movable mirror and the second interference light signal.

Subsequently, the position of the movable portion 16 in the direction A is calculated based on the second interference light signal S2 (sixth step). Hereinafter, a method of calculating the position of the movable portion 16 based on the second interference light signal S2 will be described. As illustrated in FIG. 4, when the position (optical distance) of the movable portion 16 is taken on the horizontal axis and the second interference light signal S2 is taken on the vertical axis, the point P becomes the position determination point. The point P is a crossing point between the second interference light signal S2 and the average value (DC component) thereof, and assuming that the wavelength of the second interference light signal S2 is $\lambda_L$, the point represents an optical position such as 0, $\lambda_L/2$, $\lambda_L$, $3\lambda_L/2$, $2\lambda_L$, $5\lambda_L/2$, . . . . This is because the point with the highest accuracy of position identification is a zero-crossing point in a sinusoidal wave. In this manner, with respect to the second interference light signal S2 of the wavelength $\lambda_L$, sampling points can be determined at intervals of $\lambda_L/2$. For this reason, as the wavelength (period) of the second interference light signal S2 becomes shorter, the resolution of position detection based on the second interference light signal S2 becomes higher. Ideally, an actual signal is sampled with a zero-crossing point as a trigger, and the position of the movable portion 16 may be calculated based on the sampled actual signal.

In the position detection method described above, every time the first light L2a reaches the second beam splitter 33a through the second movable mirror 31 in the returning optical path 35, a portion of the first light L2a is transmitted through the second beam splitter 33a, the remaining portion of the first light L2a is reflected by the second beam splitter 33a, and the first light reaches the second beam splitter 33a again through the second movable mirror 31 (third step). Therefore, every time the first light L2a reaches the second beam splitter 33a, the number of times of reciprocation of the first light L2a as a component along the direction A increases, and an optical path difference occurs in the first light L2a by the amount corresponding to the position of the movable portion 16 in the direction A. For this reason, when the first light L2a that has been transmitted through the second beam splitter 33a and the second light L2b are combined, the multiple interference light is generated (fourth step). A second interference light signal S2 having a wavelength of 1/p of the wavelength of the detection light L2 is extracted from the first interference light signal S1 of the multiple interference light (fifth step). The position of the movable portion 16 in the direction A is calculated based on the second interference light signal S2 (sixth step). As the wavelength (period) of the second interference light signal S2 becomes shorter, the resolution of position detection based on the second interference light signal S2 becomes higher. Therefore, by selecting the wavelength of the second interference light signal S2 to be extracted, it is possible to detect the position of the movable portion 16 with accuracy according to a request.

In addition, in the position detection method, in the fifth step, a light spectrum having a peak at each wavelength of 1/q of the wavelength of the detection light L2 is acquired by Fourier-transforming the first interference light signal S1, and the second interference light signal S2 is acquired by inverse-Fourier-transforming the light spectrum with respect to any one peak. Therefore, because the wavelength of the second interference light signal S2 becomes shorter as the wavelength of the peak used for the inverse Fourier transform becomes shorter, by selecting the peak used for the inverse Fourier transform, it is possible to detect the position of the movable portion 16 with accuracy according to a request.

As the wavelength of the peak used for the inverse Fourier transform is shorter, the accuracy of position detection is higher. However, the number of sampling points to acquire position information also increases, so that calculation load increases. In addition, because the first light L2a attenuates every time the first light L2a reaches the second beam splitter 33a, the intensity of the peak in the light spectrum tends to become smaller as the wavelength of the peak becomes shorter. In a case where the intensity of the peak is small, it may be difficult to accurately determine the sampling point in the second interference light signal S2. Therefore, the peak used for inverse Fourier transform may be selected considering these points and required accuracy.

In addition, in the position detection method, p is an integer of 2 or more. Thus, because the wavelength of the second interference light signal S2 is shorter than the wavelength of the detection light L2, it is possible to detect the position of the movable portion 16 with higher accuracy.

In addition, in the position detection method, the returning optical path 35 is formed in the second interference optical system 30A by the second movable mirror 31, the second beam splitter 33a, and the second fixed mirror 32, and the returning optical path has a rectangular shape when viewed from a direction perpendicular to the XY plane where the returning optical path 35 is located. Therefore, the returning optical path 35 can be formed in the second interference optical system 30A preferably.

In addition, in the position detection method, in the first step, the detection light L2 is split into the first light L2a and the second light L2b by the second beam splitter 33a. Therefore, for example, as compared with a case where the configuration for splitting the detection light L2 into the first light L2a and the second light L2b is provided in the second interference optical system 30A separately from the second beam splitter 33a, the configuration of the second interference optical system 30A can be simplified.

In addition, in the optical module 1 described above, the first movable mirror 21 is provided at one end portion 16a of the movable portion 16 in the direction A, and the second movable mirror 31 is provided at the other end portion 16b of the movable portion 16 in the direction A. Therefore, it is possible to move the movable portion 16 along the direction A with well balance.

In addition, in the optical module 1, the side surface of the optical block 33 made of silicon is used as the second beam splitter 33a, and the detection light L2 travels through the optical block 33. For this reason, in a case where a laser beam having a wavelength of 1.1 μm or less is used as the detection light L2, the detection light L2 is absorbed by the optical block 33. Therefore, in the optical module 1, the minimum value of the wavelength of the laser beam that can be used as the detection light L2 is 1.1 μm. Although laser light sources with wavelengths of 1.3 μm and 1.55 μm are readily available, it is difficult to increase the resolution of position detection based on interference waves of laser beams. In this respect, in the position detection method described above, for example, even in a case where a laser beam having a wavelength of 1.3 μm is used as the detection light L2, using a peak having the second longest wavelength for inverse Fourier transformation is equivalent to using a laser beam having a wavelength of 0.65 μm as the detection light L2, and thus, it is possible to sufficiently cover the wavelength range of 1.1 μm or less.

Figure 5:
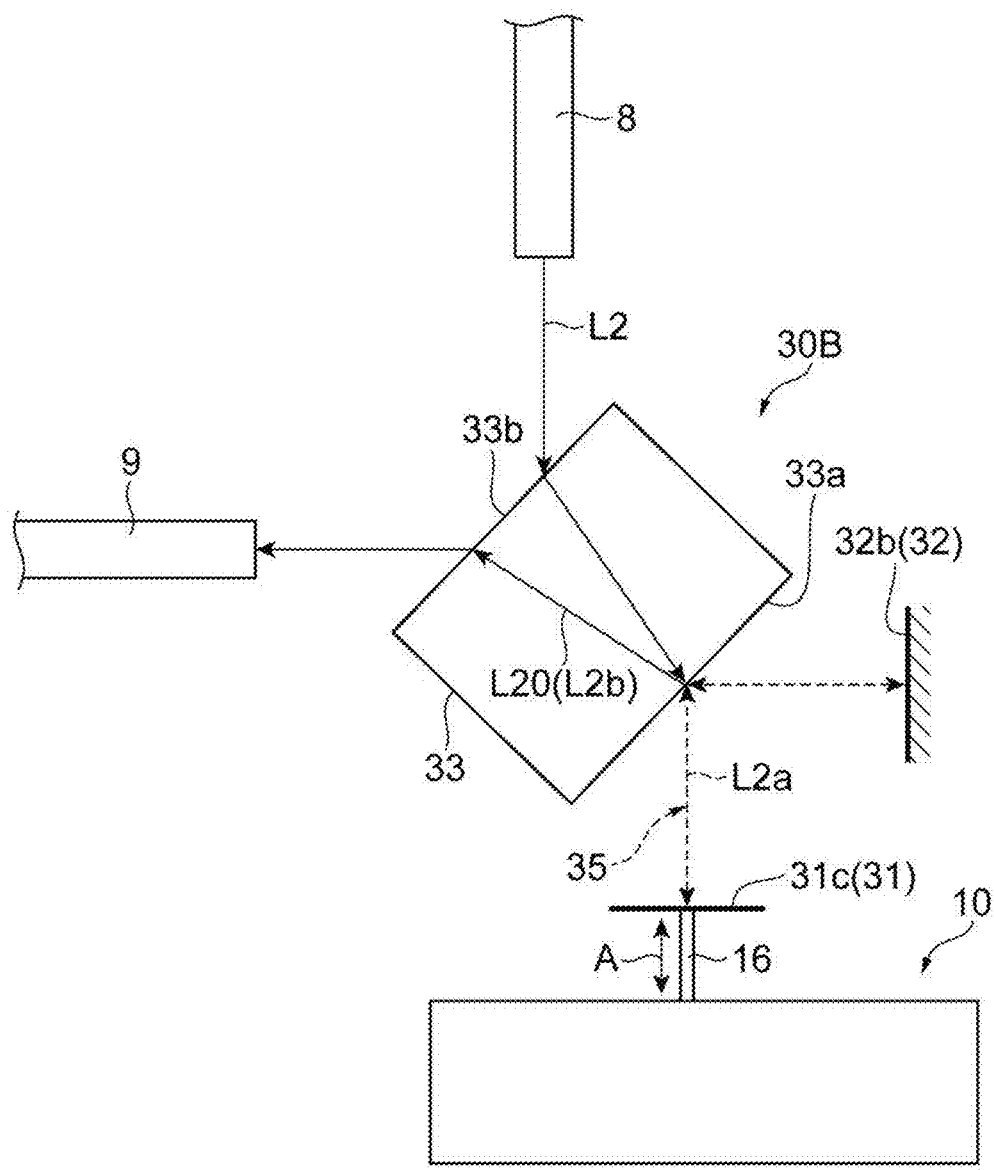
FIG. 5 is a plan view of an interference optical system according to Modified Example 1.

Although one embodiment of the present disclosure has been described above, the present disclosure is not limited to the above embodiment. For example, the second interference optical system 30B may be configured as in Modified Example 1 illustrated in FIG. 5. In the second interference optical system 30B, the second movable mirror 31 has a reflecting surface 31c perpendicular to the direction A. The second fixed mirror 32 is provided separately from the optical block 33 and has a reflecting surface 32b parallel to the direction A. The returning optical path 35 has an inverted L shape when viewed from a direction perpendicular to the XY plane. In Modified Example 1, the optical path difference constant a in the above Mathematical Formula (1) is also the value 2.

In the second interference optical system 30B, the first light L2a incident on the returning optical path 35 travels toward the second movable mirror 31 along the direction A. The first light L2a traveling toward the second movable mirror 31 along the direction A is reflected by the reflecting surface 31c of the second movable mirror 31 and returns to the second beam splitter 33a on the same optical path. The first light L2a returning to the second beam splitter 33a is split into light toward the refracting surface 33b of the optical block 33 and light toward the reflecting surface 32b of the second fixed mirror 32 by the second beam splitter 33a. After the first light L2a split toward the refracting surface 33b of the optical block 33 is refracted by the refracting surface 33b, the light returns to the detection light incident portion 8. On the other hand, the first light L2a split toward the reflecting surface 32b of the second fixed mirror 32 is reflected by the reflecting surface 32b of the second fixed mirror 32 and returns to the second beam splitter 33a on the same optical path. A portion of the first light L2a returning to the second beam splitter 33a is transmitted through the second beam splitter 33a. On the other hand, the remaining portion of the first light L2a that has reached the second beam splitter 33a travels on the returning optical path 35 and reaches the second beam splitter 33a in the same manner as described above. According to Modified Example 1, because the multiple interference light is generated in the second interference optical system 30B as in the above embodiment, by selecting the peak used for the inverse Fourier transform, it is possible to detect the position of the movable portion 16 with accuracy according to a request. In the second interference optical system 30B, every time the first light L2a reaches the second beam splitter 33a from a predetermined side (herein, the side of the reflecting surface 32b of the second fixed mirror 32) through the second movable mirror 31, a portion of the first light L2a is transmitted through the second beam splitter 33a (third step), and when the light reaches the second beam splitter 33a from a predetermined side (herein, the side of the reflecting surface 32b of the second fixed mirror 32), the first light L2a that has been transmitted through the second beam splitter 33a is combined with the second light L2b (fourth step). In this manner, when the first light L2a reflected by the second movable mirror 31 reaches the second movable mirror 31 again, in a case where the first light L2a is transmitted through the second beam splitter 33a several times, the transmitted light of the first light L2a by at least one transmission may be used for combination with the second light L2b.

Figure 6:
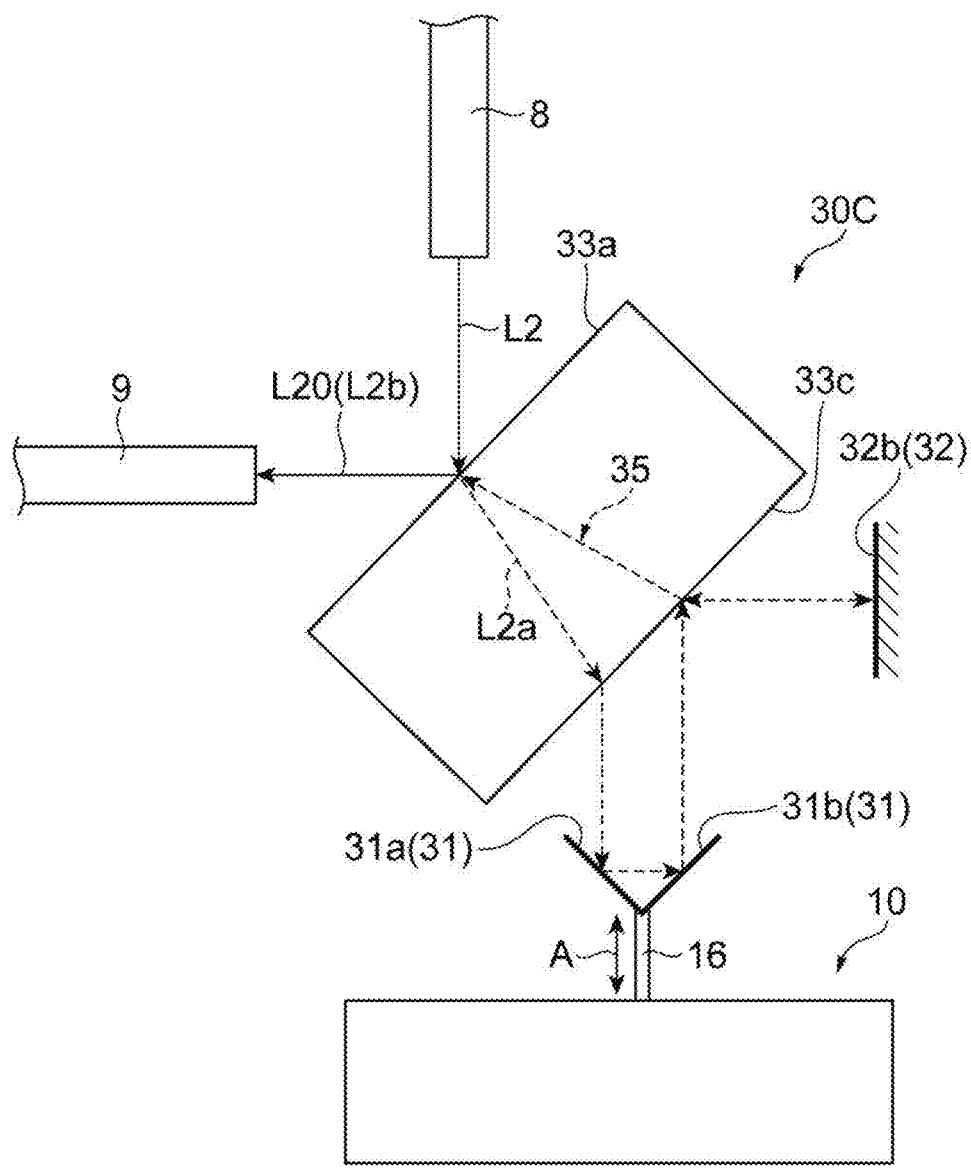
FIG. 6 is a plan view of an interference optical system according to Modified Example 2.

The second interference optical system 30C may be configured as in Modified Example 2 illustrated in FIG. 6. In the second interference optical system 30C, the second fixed mirror 32 is provided separately from the optical block 33 and has a reflecting surface 32b parallel to the direction A. The side surface of the optical block 33 facing the detection light incident portion 8 and the detection light emitting portion 9 functions as the second beam splitter 33a. The side surface of the optical block 33 facing the second beam splitter 33a functions as a refracting/reflecting surface 33c. The refracting/reflecting surface 33c extends parallel to the second beam splitter 33a. The returning optical path 35 is formed by the second movable mirror 31, the second fixed mirror 32, the second beam splitter 33a, and the refracting/reflecting surface 33c. In addition, in Modified Example 2, the optical path difference constant a in the above Mathematical Formula (1) is also the value 2.

In the second interference optical system 30C, after the first light L2a incident on the returning optical path 35 in the second beam splitter 33a travels through the optical block 33 and is refracted by the refracting/reflecting surface 33c, the light travels toward the second movable mirror 31 along the direction A. The first light L2a traveling toward the second movable mirror 31 along the direction A is sequentially reflected by the reflecting surface 31a and the reflecting surface 31b of the second movable mirror 31 and travels toward the refracting/reflecting surface 33c along the direction A. The first light L2a traveling toward the refracting/reflecting surface 33c is reflected toward the second fixed mirror 32 by the refracting/reflecting surface 33c. The first light L2a reflected toward the second fixed mirror 32 is reflected by the reflecting surface 32b of the second fixed mirror 32 and returns to the refracting/reflecting surface 33c on the same optical path. The first light L2a returning to the refracting/reflecting surface 33c is refracted by the refracting/reflecting surface 33c and reaches the second beam splitter 33a. A portion of the first light L2a that has reached the second beam splitter 33a is transmitted through the second beam splitter 33a. On the other hand, the remaining portion of the first light L2a that has reached the second beam splitter 33a travels on the returning optical path 35 and reaches the second beam splitter 33a in the same manner as described above. According to Modified Example 2 as described above, because the multiple interference light is generated in the second interference optical system 30C as in the above-described embodiment, by selecting the peak used for inverse Fourier transform, it is possible to detect the position of the movable portion 16 with accuracy according to a request.

Figure 7:
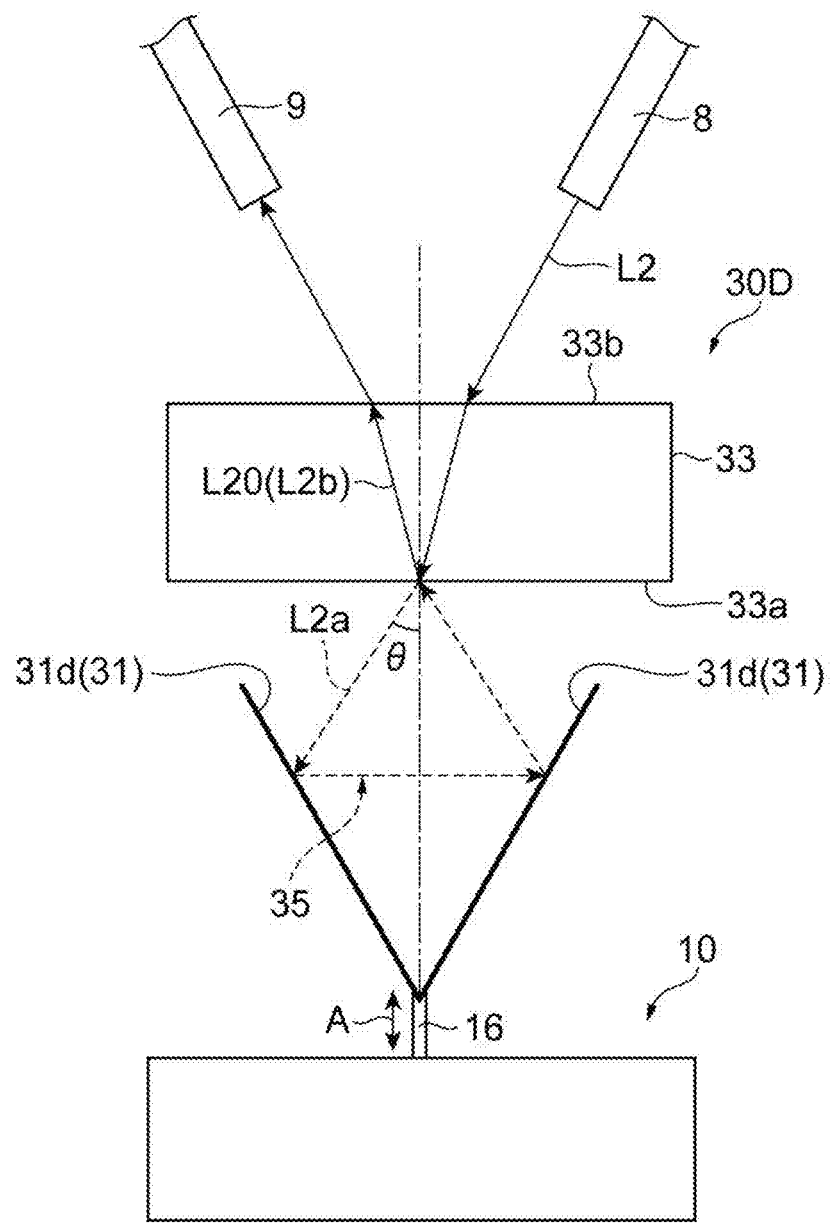
FIG. 7 is a plan view of an interference optical system according to Modified Example 3.

The second interference optical system 30D may be configured as in Modified Example 3 illustrated in FIG. 7. In the second interference optical system 30D, the second fixed mirror 32 is not provided. The second movable mirror 31 has reflecting surfaces 31d and 31d. One reflecting surface 31d is inclined by a predetermined angle with respect to the direction A, and the other reflecting surface 31d is inclined by a predetermined angle with respect to the direction A on the side opposite to the one reflecting surface 31d. The returning optical path 35 has a triangular shape when viewed from a direction perpendicular to the XY plane. Even in this case, the returning optical path 35 includes an optical path on which the detection light L2 reciprocates as a component along the direction A. In Modified Example 3, the optical path difference constant a in the above Mathematical Formula (1) is expressed as $2/\cos\theta + 2\tan\theta$ using an emission angle $\theta$ of the first light L2a from the second beam splitter 33a.

In the second interference optical system 30D, the first light L2a incident on the returning optical path 35 is sequentially reflected by the reflecting surfaces 31d and 31d of the second movable mirror 31 and reaches the second beam splitter 33a. A portion of the first light L2a that has reached the second beam splitter 33a is transmitted through the second beam splitter 33a. On the other hand, the remaining portion of the first light L2a that has reached the second beam splitter 33a travels on the returning optical path 35 and reaches the second beam splitter 33*a* in the same manner as described above. According to Modified Example 3 as described above, because the multiple interference light is generated in the second interference optical system 30D as in the above-described embodiment, by selecting the peak used for inverse Fourier transform, it is possible to detect the position of the movable portion 16 with accuracy according to a request. In addition, in Modified Example 3, because the optical path difference constant a is larger than that in the above embodiment, the optical path difference occurring in the first light L2*a* is increased. This is equivalent to using light having a shorter wavelength for the detection light L2, which denotes that the detection accuracy of the position of the movable portion 16 is high.

Figure 8:
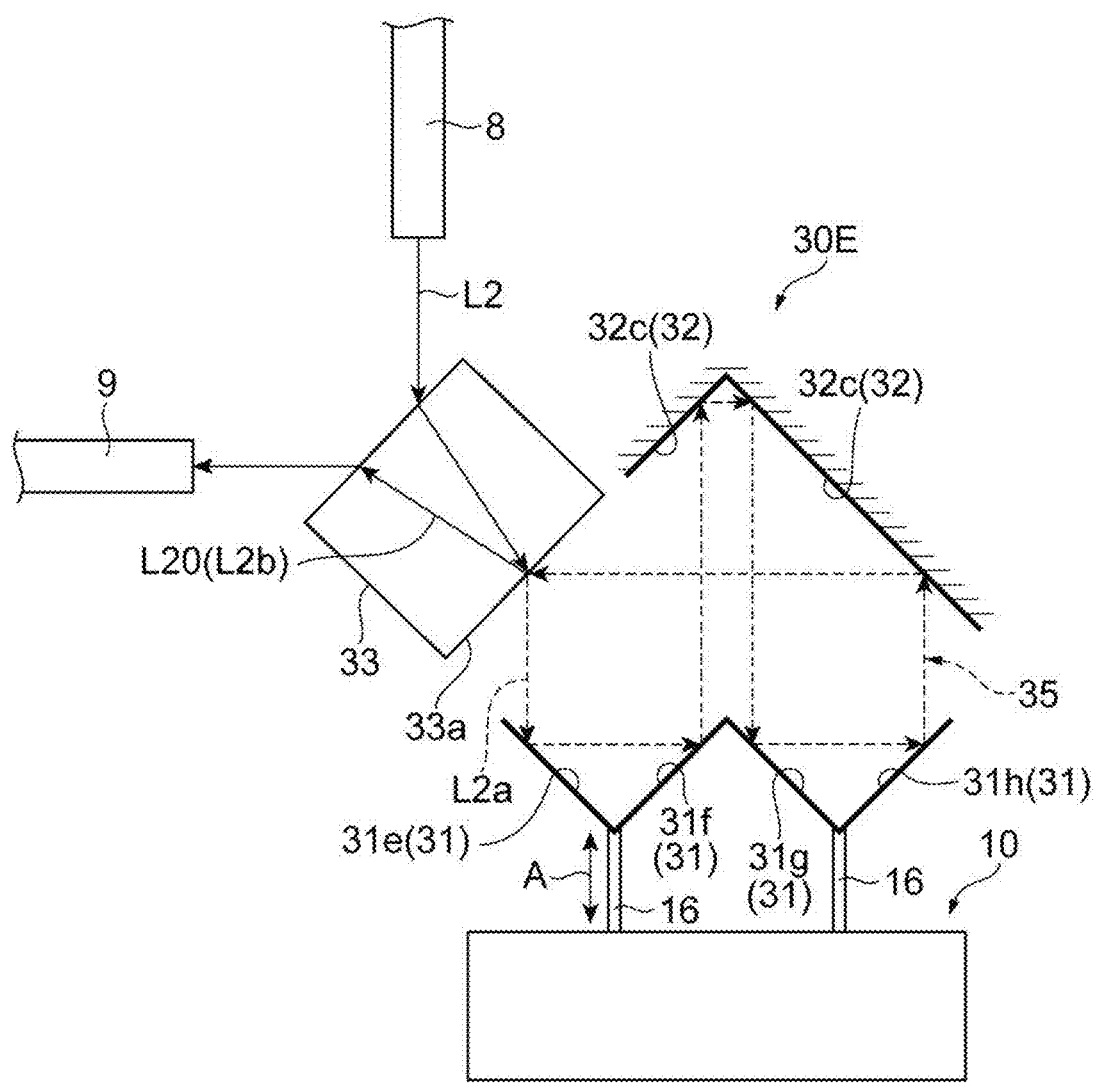
FIG. 8 is a plan view of an interference optical system according to Modified Example 4.

The second interference optical system 30E may be configured as in Modified Example 4 illustrated in FIG. 8. In Modified Example 4, the movable portion 16 is configured with two rod-like portions that move together. In the second interference optical system 30E, the second movable mirror 31 has reflecting surfaces 31*e*, 31*f*, 31*g*, and 31*h*. The reflecting surface 31*e* is inclined by 45 degrees with respect to the direction A. The reflecting surface 31*f* is provided adjacent to the reflecting surface 31*e* and is inclined by 45 degrees with respect to the direction A on the side opposite to the reflecting surface 31*e*. The reflecting surface 31*g* is provided adjacent to the reflecting surface 31*f* on the side opposite to the reflecting surface 31*e* and is inclined by 45 degrees with respect to the direction A on the side opposite to the reflecting surface 31*f*. The reflecting surface 31*h* is provided adjacent to the reflecting surface 31*g* on the side opposite to the reflecting surface 31*f* and is inclined by 45 degrees with respect to the direction A on the side opposite to the reflecting surface 31*g*.

The second fixed mirror 32 is provided separately from the optical block 33 and has reflecting surfaces 32*c* and 32*c*. One reflecting surface 32*c* is inclined by 45 degrees with respect to the direction A, and the other reflecting surface 32*c* is inclined by 45 degrees with respect to the direction A on the side opposite to the one reflecting surface 32*c*. The returning optical path 35 includes an optical path on which the light reciprocates twice along the direction A. In Modified Example 4, because the first light L2*a* reciprocates twice along the direction A every time the first light reaches the second beam splitter 33*a*, the optical path difference constant a in the above Mathematical Formula (1) is the value 4.

In the second interference optical system 30E, the first light L2*a* incident on the returning optical path 35 is sequentially reflected by the reflecting surfaces 31*e* and 31*f* of the second movable mirror 31 and travels toward the second fixed mirror 32 along the direction A. The first light L2*a* traveling toward the second fixed mirror 32 along the direction A is sequentially reflected by the reflecting surfaces 32*c* and 32*c* of the second fixed mirror 32 and travels toward the second movable mirror 31 along the direction A. The first light L2*a* traveling toward the second movable mirror 31 along the direction A is sequentially reflected by the reflecting surfaces 31*g* and 31*h* of the second movable mirror 31 and travels toward the second fixed mirror 32 along the direction A. The first light L2*a* traveling toward the second fixed mirror 32 along the direction A is reflected by the reflecting surface 32*c* of the second fixed mirror 32 and reaches the second beam splitter 33*a*. A portion of the first light L2*a* that has reached the second beam splitter 33*a* is transmitted through the second beam splitter 33*a*. On the other hand, the remaining portion of the first light L2*a* that has reached the second beam splitter 33*a* travels on the returning optical path 35 and reaches the second beam splitter 33*a* in the same manner as described above. According to Modified Example 4, because the multiple interference light is generated in the second interference optical system 30E as in the above-described embodiment, by selecting the peak used for the inverse Fourier transform, it is possible to detect the position of the movable portion 16 with accuracy according to a request. In addition, in Modified Example 4, because the optical path difference constant a is larger than that in the above-described embodiment, the optical path difference occurring in the first light L2*a* is increased. This is equivalent to using light having a shorter wavelength for the detection light L2, which denotes that the detection accuracy of the position of the movable portion 16 is high.

Figure 9:
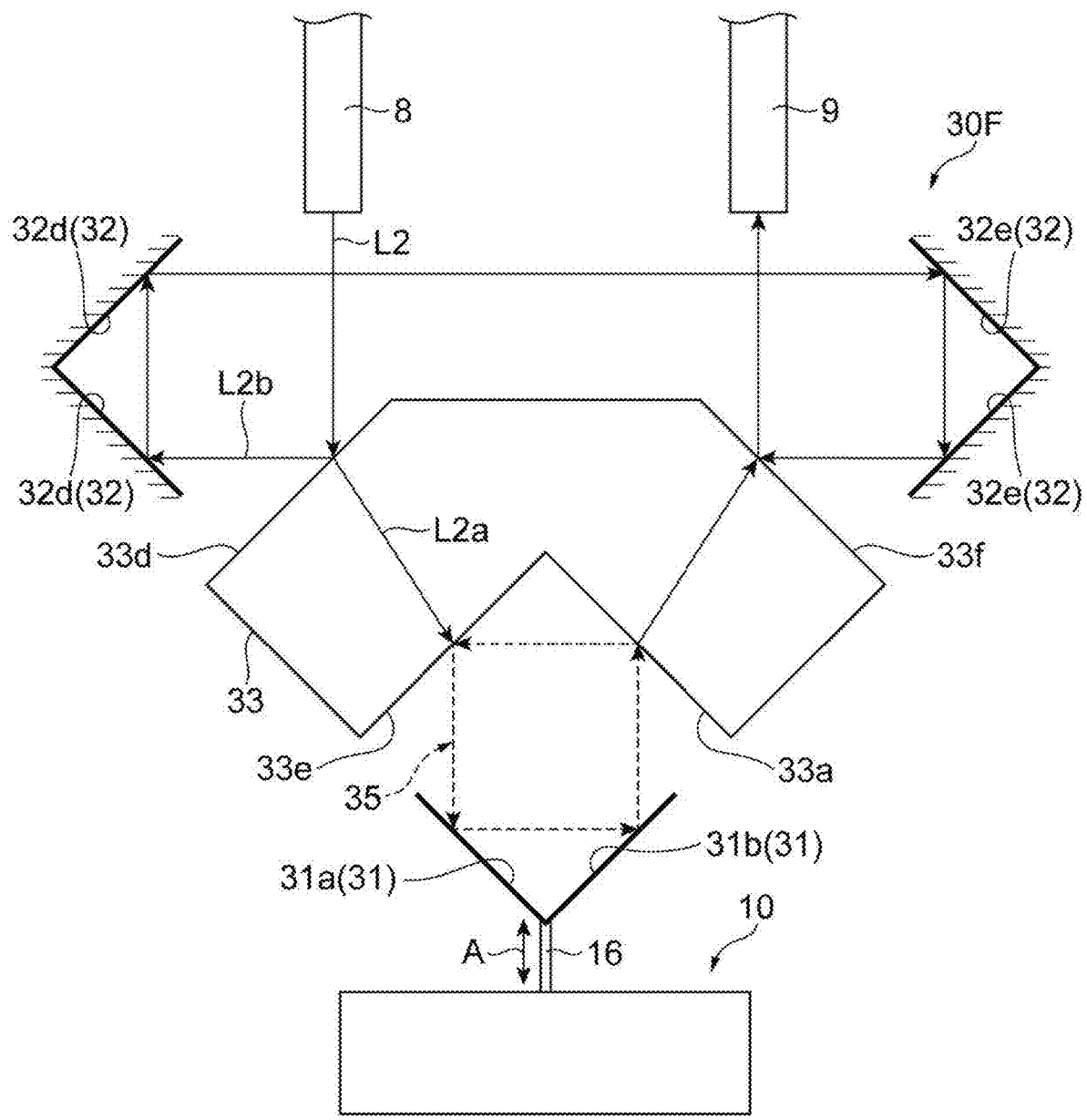
FIG. 9 is a plan view of an interference optical system according to Modified Example 5.

The second interference optical system 30F may be configured as in Modified Example 5 illustrated in FIG. 9. In the second interference optical system 30F, a pair of second fixed mirrors 32 are provided separately from the optical block 33. One of the second fixed mirrors 32 has reflecting surfaces 32*d* and 32*d*. One reflecting surface 32*d* is inclined by 45 degrees with respect to the direction A, and the other reflecting surface 32*d* is inclined by 45 degrees with respect to the direction A on the side opposite to the one reflecting surface 32*d*. The other second fixed mirror 32 has reflecting surfaces 32*e* and 32*e*. One reflecting surface 32*e* is inclined by 45 degrees with respect to the direction A, and the other reflecting surface 32*e* is inclined by 45 degrees with respect to the direction A on the side opposite to the one reflecting surface 32*e*. The reflecting surfaces 32*d* and 32*d* and the reflecting surfaces 32*e* and 32*e* face each other in a direction perpendicular to the direction A.

The side surface of the optical block 33 facing the detection light incident portion 8 functions as a third beam splitter 33*d*. In other words, the position of the third beam splitter 33*d* is fixed. The third beam splitter 33*d* is a surface perpendicular to the XY plane and is inclined by 45 degrees with respect to the direction A. The side surface of the optical block 33 facing the third beam splitter 33*d* functions as a refracting/reflecting surface 33*e*. The refracting/reflecting surface 33*e* extends parallel to the third beam splitter 33*d*. The side surface of the optical block 33 facing the second beam splitter 33*a* functions as a refracting/reflecting surface 33*f*. The refracting/reflecting surface 33*e* extends parallel to the second beam splitter 33*a*. The returning optical path 35 is formed by the second movable mirror 31, the second beam splitter 33*a*, and the refracting/reflecting surface 33*e*. In addition, in Modified Example 5, the optical path difference constant a in the above Mathematical Formula (1) is the value 2.

In the second interference optical system 30F, the detection light L2 incident on the second interference optical system 30F through the detection light incident portion 8 is split into the first light L2*a* and the second light L2*b* by the third beam splitter 33*d*. The first light L2*a* travels through the optical block 33 and is incident on the returning optical path 35 along the direction A on the refracting/reflecting surface 33*e*. The first light L2*a* incident on the returning optical path 35 on the refracting/reflecting surface 33*e* is sequentially reflected by the reflecting surface 31*a* and the reflecting surface 31*b* of the second movable mirror 31 and reaches the second beam splitter 33*a* along the direction A. A portion of the first light L2*a* that has reached the second beam splitter 33*a* is transmitted through the second beam splitter 33*a* and reaches the refracting/reflecting surface 33*f*. On the other hand, the remaining portion of the first light L2*a* that has reached the second beam splitter 33*a* travels toward the refracting/reflecting surface 33e, travels on the returning optical path 35 in the same manner as described above, and reaches the second beam splitter 33a.

The second light L2b split by the third beam splitter 33d travels toward one of the second fixed mirrors 32 along a direction perpendicular to the direction A. The second light L2b that has traveled to one of the second fixed mirrors 32 along the direction perpendicular to the direction A is sequentially reflected by the reflecting surfaces 32d and 32d of the second fixed mirror 32 and travels toward the other second fixed mirror 32 along the direction perpendicular to the direction A. The second light L2b that has traveled to the other second fixed mirror 32 along the direction perpendicular to the direction A is sequentially reflected by the reflecting surfaces 32e and 32e of the other second fixed mirror 32 and reaches the refracting/reflecting surface 33f. The first light L2a that has been transmitted through the second beam splitter 33a and the second light L2b are combined on the refracting/reflecting surface 33f and become the interference light L20 of the detection light L2. According to Modified Example 5, because the multiple interference light is generated in the second interference optical system 30F as in the above embodiment, by selecting the peak used for the inverse Fourier transform, it is possible to detect the position of the movable portion 16 with accuracy according to a request.

In the above embodiment, the actuator 10 is not limited to an electrostatic actuator, but for example, a piezoelectric actuator, an electromagnetic actuator, or the like may be employed. A laser light source that outputs the detection light L2 and a light detector that detects the interference light L20 of the detection light L2 may be mounted on the optical module 1. Depending on the required accuracy, in the sixth step, the position of the movable portion 16 in the direction A may be calculated based on the second interference light signal S2 acquired by inverse-Fourier-transforming the light spectrum with respect to the peak having the longest wavelength, (in other words, p may be 1). The returning optical path 35 may have any shape such as a pentagon, a number-8 shape when viewed from a direction perpendicular to the XY plane. In a case where the returning optical path 35 has a rectangular annular shape and has a pair of optical paths parallel to the direction A as in the above embodiment, the configuration of the second interference optical system 30A is simplified, and the loss of the detection light L2 is reduced. In addition, the calculation formula is simplified, and the calculation load is reduced.

In the above embodiment, a light spectrum having a peak at each wavelength of 1/q of the wavelength of the detection light L2 is acquired by Fourier transform of the first interference light signal S1, and the second interference light signal S2 having a wavelength of 1/p of the wavelength of the detection light L2 is acquired by inverse Fourier transform. However, by using a method different from the above method, the second interference light signal S2 may be extracted from the first interference light signal S1. For example, the second interference light signal S2 is extracted from the first interference light signal S1 by performing a convolution operation on the first interference light signal S1 with a predetermined weight function (for example, a sinc function or an exponential function). According to this method, the calculation time can be shortened as compared with the method using Fourier transform and inverse Fourier transform. Alternatively, on the circuit, a component for filtering the first interference light signal S1 may be provided on the downstream side of the light detector for detecting the interference light L20, so that the second interference light signal S2 can be extracted from the first interference light signal S1. According to the method using the Fourier transform and the inverse Fourier transform, it is possible to extract the second interference light signal S2 from the first interference light signal S1 with good accuracy.

What is claimed is:

1. A position detection method for detecting a position of a movable portion which moves along a predetermined direction, comprising:
    splitting detection light into first light and second light in an interference optical system including a movable mirror coupled to the movable portion and a beam splitter having a fixed position, wherein the first light is incident on a circulating optical path formed in the interference optical system by the movable mirror and the beam splitter, and a portion of the first light is transmitted through the beam splitter and a remaining portion of the first light is reflected by the beam splitter to reach the beam splitter through the movable mirror every time the first light reaches the beam splitter through the movable mirror in the circulating optical path;
    combining the first light transmitted through the beam splitter from the circulating optical path and the second light to generate multiple interference light in the interference optical system;
    extracting a second interference light signal having a wavelength of 1/p (p is a natural number) of a wavelength of the detection light from a first interference light signal of the multiple interference light; and
    calculating the position of the movable portion in the predetermined direction based on the second interference light signal.

2. The position detection method according to claim 1, wherein, in extracting the second interference light signal, a light spectrum having a peak at each wavelength of 1/q (q is a natural number) wavelength of the detection light is acquired by Fourier-transforming the first interference light signal, and the second interference light signal is acquired by inverse-Fourier-transforming the light spectrum with respect to one of the peaks.

3. The position detection method according to claim 1, wherein p is an integer of 2 or more.

4. The position detection method according to claim 1,
    wherein the interference optical system further includes a fixed mirror having a fixed position, and
    wherein the circulating optical path is formed in the interference optical system by the movable mirror, the beam splitter, and the fixed mirror and has a rectangular shape when viewed from a direction perpendicular to a plane where the circulating optical path is located.

5. The position detection method according to claim 1, wherein, the detection light is split into the first light and the second light by the beam splitter.

6. An optical module comprising:
    a movable portion which moves along a predetermined direction; and
    an interference optical system including a movable mirror coupled to the movable portion and a beam splitter having a fixed position,
    wherein, in the interference optical system, a circulating optical path is formed by the movable mirror and the beam splitter, detection light is split into first light and second light, the first light is incident on the circulating optical path, every time the first light reaches the beam splitter through the movable mirror, a portion of the first light is transmitted through the beam splitter and a remaining portion of the first light is reflected by the beam splitter to reach the beam splitter through the movable mirror, and the first light transmitted through the beam splitter from the circulating optical path and the second light are combined to generate multiple interference light.

7. The optical module according to claim 6,
wherein the interference optical system further includes a fixed mirror having a fixed position, and
wherein the circulating optical path is formed in the interference optical system by the movable mirror, the beam splitter, and the fixed mirror and has a rectangular shape when viewed from a direction perpendicular to a plane where the circulating optical path is located.

8. The optical module according to claim 6, wherein in the interference optical system, the detection light is split into the first light and the second light by the beam splitter.

9. The optical module according to claim 6, further comprising a measurement interference optical system including a measurement mirror coupled to the movable portion,
wherein the measurement mirror is provided at one end portion of the movable portion in the predetermined direction, and
wherein the movable mirror is provided at the other end portion of the movable portion in the predetermined direction.

\* \* \* \* \*